United States Patent [19]

Levin

[11] Patent Number: 4,713,349

[45] Date of Patent: Dec. 15, 1987

[54] TEMPLET FOR SIMULTANEOUS SCREENING OF SEVERAL ANTIBODIES AND METHOD OF USING THE SAME

[75] Inventor: Andrew E. Levin, Cambridge, Mass.

[73] Assignee: Wisconsin Alumni Research Foundation, Madison, Wis.

[21] Appl. No.: 705,094

[22] Filed: Feb. 25, 1985

[51] Int. Cl.$^4$ .................... B01L 9/00; G01N 33/543; G01N 33/548; G01N 33/559

[52] U.S. Cl. .................... 436/515; 422/104; 436/518; 436/530; 436/548; 436/809

[58] Field of Search ................. 422/68, 104; 436/501, 436/515, 518, 530, 548, 809

[56] References Cited

U.S. PATENT DOCUMENTS

| | | |
|---|---|---|
| 3,378,481 | 4/1968 | Saravis et al. |
| 3,645,687 | 2/1972 | Nerenberg |
| 3,922,203 | 11/1975 | Aldridge, Jr. et al. |
| 3,925,166 | 12/1975 | Blume |
| 4,018,662 | 4/1977 | Ruhenstroth-Bauer et al. |
| 4,031,197 | 6/1977 | Marinkovich |
| 4,130,471 | 12/1978 | Grunbaum |
| 4,136,007 | 1/1979 | Fujimori |
| 4,151,065 | 4/1979 | Kaplan et al. |
| 4,234,404 | 11/1980 | Satoh |
| 4,294,684 | 10/1981 | Serwer |
| 4,385,974 | 5/1983 | Shevitz |
| 4,415,418 | 11/1983 | Turre et al. |
| 4,416,761 | 11/1983 | Brown et al. |
| 4,431,506 | 2/1984 | Gorman, Jr. et al. |
| 4,443,319 | 4/1984 | Chait et al. |
| 4,452,901 | 6/1984 | Gordon et al. ............ 436/530 |

OTHER PUBLICATIONS

V. C. W. Tsang et al, *Meth. Enzymol.*, 92, 377–391, 1983.
W. J. Herbert et al, *Dictionary of Immunology*, 3rd ed., Blackwell Scientific Publications, Oxford, 1985, pp. 114, 234 and 235.
Elizabeth Smith et al., "Monoclonal Antibody Screening: Two Methods Using Antigens Immobilized on Nitrocellulose", Analytical Biochemistry 138, pp. 119–124 (1984).
Advertisement published by Bio-Rad, Inc. announcing "New Incubation Tray".

*Primary Examiner*—Sidney Marantz
*Assistant Examiner*—David A. Saunders
*Attorney, Agent, or Firm*—Isaksen, Lathrop, Esch, Hart & Clark

[57] ABSTRACT

A templet (10) is provided having a lower plate (11) which receives a carrier sheet having antigens immobilized thereon as transferred from an electrophoresis gel. An upper plate (12) having a plurality of parallel channels (22) formed therein, is placed over the lower plate such that the channels lie over the carrier sheet. The two plates (11, 12) are then pressed tightly together, as by engagement with screws (16) at the periphery of the plates. A bridge bar (28) extends over the central portion of the plate and pressure screws (30) are mounted to the bridge bar in position to engage and apply pressure to the top surface of the upper plate (12). Various antibody containing liquids are introduced into the various channels through holes (25) extending to the ends of the channels; the solutions are allowed to remain in contact with the antigens on the carrier sheet for a period of time, after which the liquid is withdrawn from the channels, and the plates separated. The entire carrier sheet is subsequently exposed to tracer antibodies labeled radioactively or otherwise. The carrier sheet so treated shows a series of parallel vertical stripes, in each of which those horizontal antigen bands reactive with the particular antibody applied to the stripe are indicated. An antigen, or mixture of antigens, may thus be screened with many different antibodies simultaneously, and the user may compare the relative positions of antibody-labeled antigen bands on a single carrier sheet.

18 Claims, 8 Drawing Figures

TEMPLET FOR SIMULTANEOUS SCREENING OF SEVERAL ANTIBODIES AND METHOD OF USING THE SAME

This invention was made with government support under NIH Grant No. GM31098 awarded by the Department of Health and Human Services. The Government has certain rights in this invention.

FIELD OF THE INVENTION

This invention pertains generally to devices and techniques used in analytical biochemistry and particularly to the screening and analysis of antibodies.

BACKGROUND OF THE INVENTION

Selection of monoclonal antibodies which bind specific antigens presents a major analytical challenge when the antigen source is impure. The gel electrophoresis procedure is often used in analyzing the antigens present. In this procedure, a gel, commonly polyacrylamide, is poured into a rectangular plate and the protein or antigen mix to be analyzed is applied to the top of the gel. A strong voltage is then applied between the top and bottom of the gel to pull the charged proteins through the gel which, after a period of time, results in a separation of the proteins present into separate bands spaced between the top and bottom of the gel. A carrier sheet, typically a nitrocellulose membrane, is then brought into contact with the surface of the gel causing the proteins to adhere to and become immobilized on the surface of the nitrocellulose carrier sheet. In the present typical immunoblotting technique, the sheet of nitrocellulose with the proteins adhering thereto is cut up into several strips and each strip is incubated for a period of time in a solution containing a particular antibody of a first type, designated primary antibody. If the primary antibody recognizes one of the bands of protein on the strip, it will bind to it. The strip may then be placed in a solution containing a secondary antibody which recognizes and binds to the primary antibody, with the secondary antibody having a tracer (e.g., a radioactive isotope) carried therewith. If a radioactive isotope tracer is used, a film sensitive to the radiation from the isotope may be laid over the strip to reveal the location on the strip at which the antibodies have bound. In this way, the proteins to which the particular antibodies are binding can be determined.

The standard immunoblotting technique briefly described above can thus be very time consuming and tedious, particularly if tens or hundreds of antibodies are to be tested. The technique is also prone to errors, since the separate strips may become mixed up or misidentified, and the strips themselves can tend to shrink or expand, making it difficult to compare the position of the bands detected on separate strips. In particular, selection of hybridoma cultures producing monoclonal antibodies makes efficient and rapid screening of large numbers of cultures highly desirable. Usually, immunoblotting is the only method by which the monoclonal antibodies may be selected if the antigen of interest is not purified. In the early stages of the selection of hybridomas, colonies must be screened within days to ensure cell viability. If the screening method is inefficient at this stage, extended cell culture work is required. More efficient screening techniques permit the screening of more hybridomas, increasing the probability of success in selecting the desirable antibody producing lines. However, present immunoblotting screening is inefficient for several reasons. First, for each hybridoma to be tested, a separate strip of nitrocellulose must be processed through the many steps of the procedure. Second, during the early stages of hybridoma growth, the quantity of antibody available for screening is extremely limited, and individual strips of nitrocellulose must be incubated with the limited quantity of antibody, a difficult proposition. Third, all of the individual strips of nitrocellulose must be compared after completion of the procedure, which is time consuming and is subject to the errors described above.

SUMMARY OF THE INVENTION

The templet of the present invention provides for the simultaneous screening of many antibodies on a single carrier sheet on which proteins have been immobilized. The templet allows very small volumes of antibody solution to be used (e.g., as low as 100 microliters), making immunoblot screening of microtiter plate hybridoma cultures practical. The results of the screening may be obtained within several hours, providing the researcher with the information to immediately select hybridomas for expansion and to discard useless colonies. The carrier sheet remains intact during the treatment with the various antibody solutions, allowing the researcher to view the entire sheet and accurately compare the position of bands as marked by tracers. Polyclonal antibodies may also be tested for specificity and titer using the templet.

The templet includes a lower plate having a top surface with flat central area sized to receive the carrier sheet, an upper plate with several parallel channels formed therein extending over the central area of its bottom surface and with flat land areas between the channels, large holding screws which thread through the upper and lower plates at peripheral areas to draw the inner surfaces of the plates tightly together, and a bridge bar which is engaged to the upper plate at peripheral areas and which spans the central area. One or more pressure screws are provided which thread through the bridge bar into engagement with the top surface of the upper plate over the central area thereof to provide a means for applying force to the central area of the upper plate above the parallel channels to press the plates together in this area.

In using the templet, a carrier sheet (e.g., a nitrocellulose membrane), upon which protein bands have been transferred from a gel electrophoresis preparation, is laid onto the central area of the lower plate with the protein coated side of the carrier sheet facing upwardly. The upper plate is then placed down onto the lower plate such that the channels extend over the carrier sheet aligned with the direction of protein transport during electrophoresis. Screws are then threaded through openings in the upper plate and into engagement with threaded bores in the lower plate at the peripheral areas of the plates to hold the two tightly together. The bridge bar is then engaged with screws to the upper and lower plates, and large screws are then turned through threaded holes in the bridge bar into contact with the central area of the top surface to tightly press down thereon. The upper and lower plates are preferably formed of a strong and hard but somewhat flexible material, e.g., acrylic plastic, which allows the mating surfaces of the upper and lower plates to be clamped very tightly over the carrier sheet, preventing the migration of fluid between the channels. Various primary antibody solutions are then injected into each of the channels and allowed to incubate for a selected period of time. The upper plate is then removed, and the carrier sheet is removed from its position on the lower plate. The carrier sheet is then washed and incubated in a tray with tracer tagged secondary antibodies. Finally, excess tracer tagged antibodies are washed off the carrier sheet, and photographic film or other means are applied to the sheet to detect the tracer. The tracer thus reveals the location of bands of antigen which bind to the primary antibodies, and which are distributed in vertical stripes on the carrier sheet, corresponding in location to the channels in the upper plate.

Further objects, features, and advantages of the present invention will be apparent from the following detailed description when taken in conjunction with the accompanying drawings showing the preferred embodiment of a templet in accordance with the invention.

DESCRIPTION OF THE PREFERRED EMBODIMENT

Figure 1:
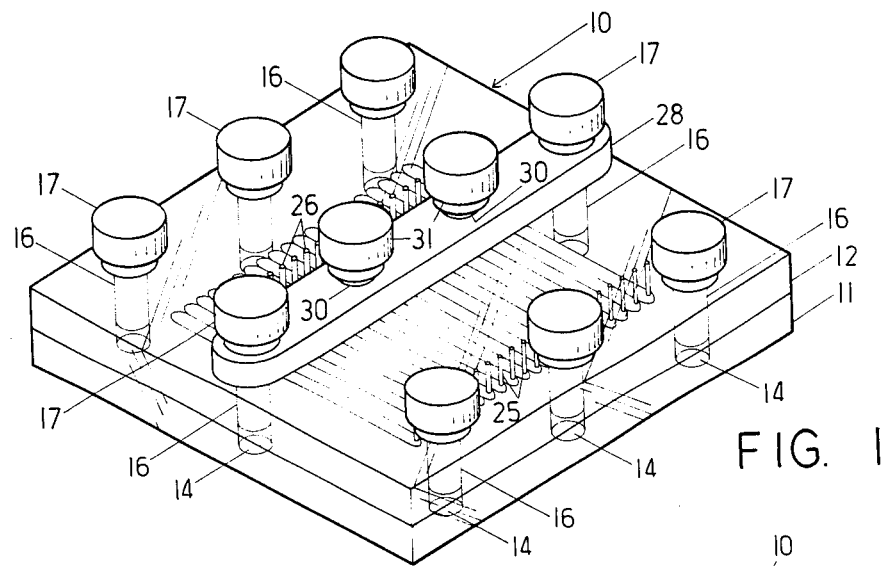
FIG. 1 is a perspective view of an assembled screening templet in accordance with the invention.
Figure 2:
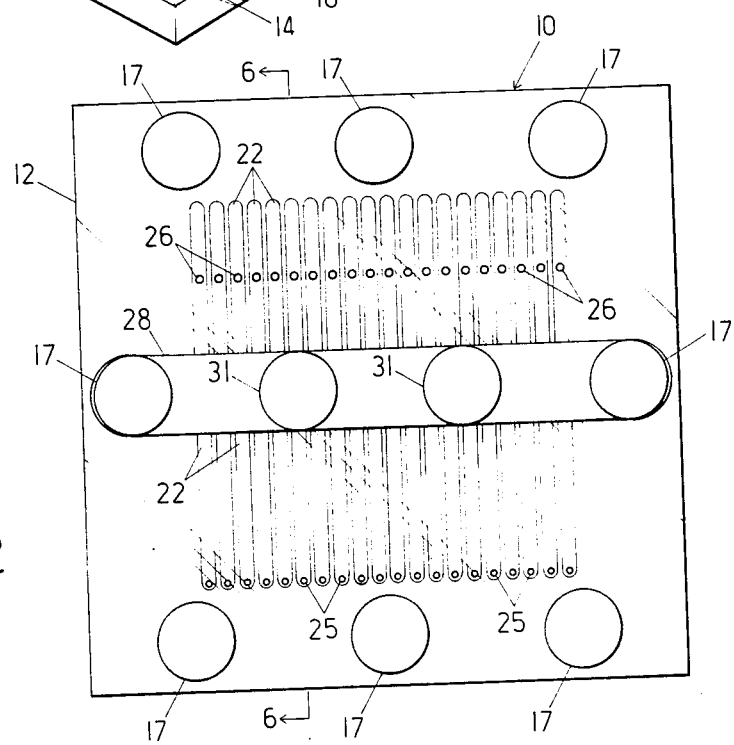
FIG. 2 is a top plan view of the templet of FIG. 1.
Figure 3:
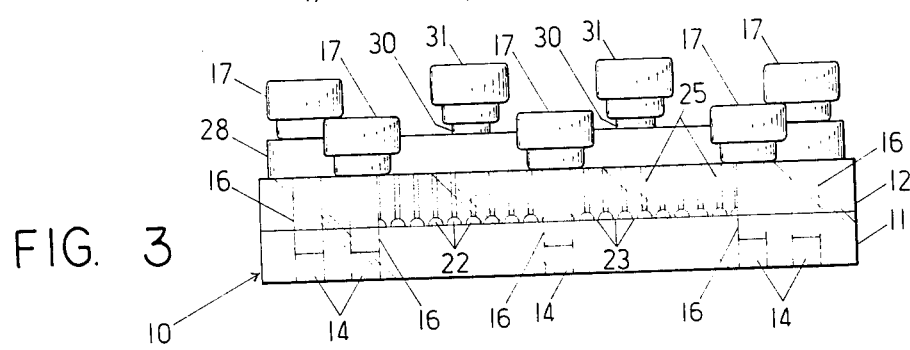
FIG. 3 is a front elevation view of the templet of FIG. 1.

With reference to the drawings, a templet in accordance with the invention for use in screening antibodies is shown generally at 10 in FIG. 1. The templet 10 has a generally rectangular lower plate 11 and a similarly sized and shaped upper plate 12. The plates 11 and 12 are shown in FIG. 1 in their assembled, mating position as they would be when utilized to hold a carrier sheet between them. The plates are preferably formed of a substantially rigid yet somewhat flexible plastic material, such as acrylic plastic (e.g., as sold under the trademark Plexiglass), which is also resistant to common biochemical reagents, and the material forming the plates may thus be transparent as illustrated in the drawings. A series of threaded holes 14 are formed in the lower plate 11 in the peripheral areas thereof, and corresponding openings 15, either threaded or unthreaded, are formed in the upper plate 12. Large holding screws 16 having expanded knurled heads 17 (for convenient grasping by a user) are threaded through the holes 15 and into the threaded holes 14 to draw the plates 11 and 12 tightly together when in use. The expanded heads engage the top surface of the upper plate and apply force thereto as the screws are turned in to draw the upper plate 12 toward the lower plate 11. These screws 16 are preferably formed of a plastic material, such as acetal plastic (e.g., as sold under the trademark Delrin) which can be engaged with the plates 11 and 12 without damaging the plastic material of these plates.

Figure 4:
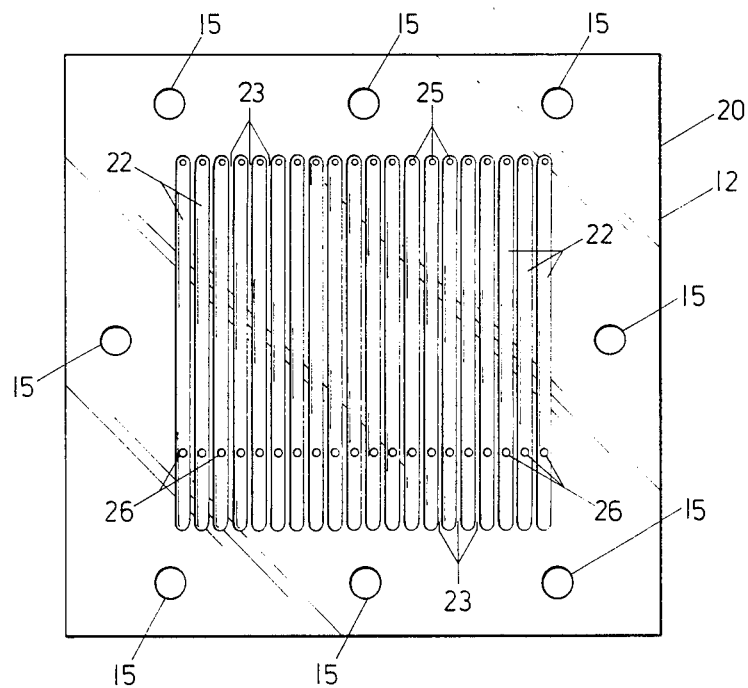
FIG. 4 is a plan view of the bottom face of the upper plate portion of the templet of FIG. 1.
Figure 5:
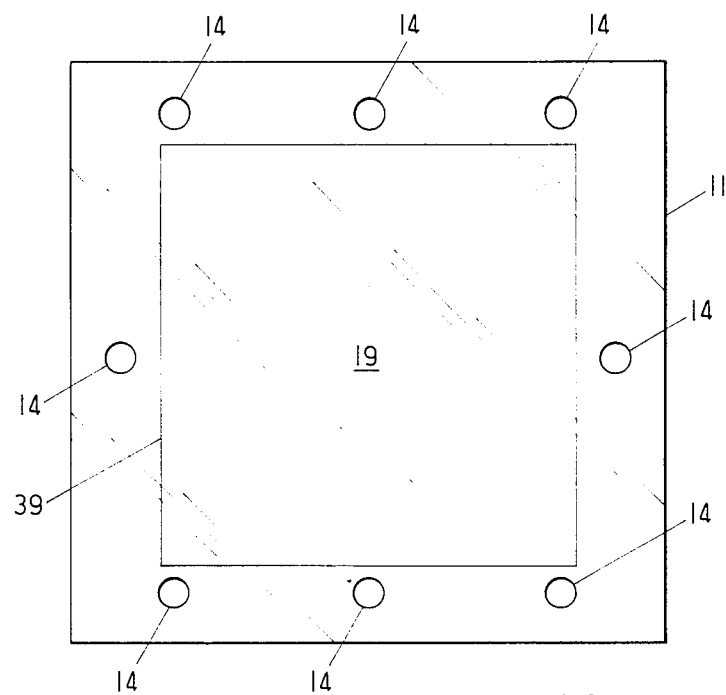
FIG. 5 is a plan view of the top face of the lower plate portion of the templet of FIG. 1.
Figure 6:
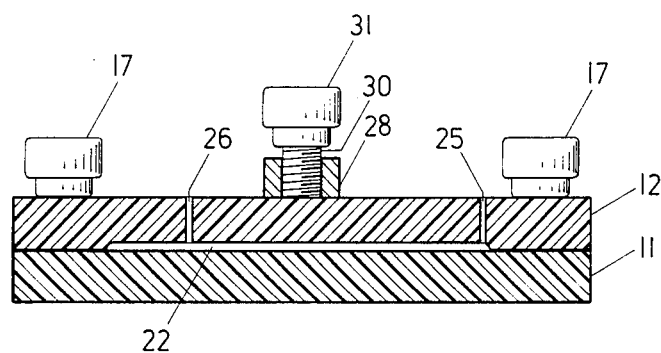
FIG. 6 is a cross-sectional view of the templet of FIG. 1 taken generally along the lines 6—6 of FIG. 2.

With particular reference to FIG. 5—a view of the top or inner surface of the bottom plate 11—the central area 19 of the inner or top surface of the lower plate 11 is smooth and flat. In this area, a carrier sheet of nitrocellulose with proteins immobilized thereon may be laid flat. The screw holes 14 are all located in the peripheral areas of the plate 11 outside of the central area 19 so as not to interfere with the placement of the carrier sheet. Correspondingly, as shown in FIG. 4, the screw holes 15 in the upper plate 12 are all located in the peripheral areas of the plate outside of the central area of the bottom or inner surface of the upper plate 12. In this central area a plurality of channels 22 are formed in the inner surface 20 of the top plate, such as by milling of preformed solid plastic or by a thermoplastic molding operation. Between the elongated channels 22 are land areas 23 which are coplanar with the outer areas of the bottom surface 20 and which separate the channels 22 from each other. Small holes 25 are formed (as by drilling) in the upper plate 12 and extend from its top surface into each of the channels at one of the ends thereof. Another set of holes 26 extend from the top surface of the upper plate 12 to the channels at a position toward the opposite ends thereof.

An elongated bridge bar 28 is formed to have adequate resistance to bending and is preferably substantially rectangular in shape with a flat bottom surface which allows it to lie substantially flat across the top surface of the upper plate. The bridge bar 28 is mounted in position on the top surface of the upper plate 12 with holding screws 16 which thread down into the holes 14 and 15 in the plates at peripheral positions on the plates to hold the bridge bar 28 firmly against the top surface of the upper plate. Pressure screws 30 having knurled heads 31 are then turned through threaded holes in the bridge bar 28 until the bottoms of the screws 30 come into contact with the top surface of the upper plate 12. As the user turns the screws 30 to tighten them against the plate, the screws apply a downward pressure on the top surface of the upper plate, depressing the central area of the upper plate to tightly engage the carrier sheet (not shown) between the upper and lower plates.

As an example of a templet 10 of the form illustrated in FIGS. 1-6, the plates 11 and 12 may be machined from Plexiglass (e.g., approximately 8 inches on a side, ¾ inch thick) with the opposite surfaces of each plate being machined flat. Three-eighths inch diameter screw holes 14 and 15 may be drilled into each plate with the holes 14 in the lower plate being threaded. Twenty channels (e.g., 3/16 inch wide, 1/10 inch deep with a U-shaped bottom, 4⅜ inch long, separated by 1/16 inch land areas 23) can be formed by milling the bottom or inner surface of the upper plate. The holes 25 and 26 (e.g., 3/32 inch diameter) may then be drilled through the upper plate and are preferably tapered so that a standard disposable plastic pipette tip (1 milliliter capacity) may be easily inserted for the introduction and withdrawal of antibody solutions and washing liquids into the channels 22. The bridge bar 28 may be formed of aluminum (e.g., 1 inch wide, ½ inch thick) spanning the width of the templet. This bar may be drilled with four holes, the outer two not being threaded and readily passing the screws 16 and the inner ones being threaded to accept and engage the screws 30.

After the preparative style electrophoresis of the antigen source is completed, antigens are transferred from the polyacrylamide gel to a nitrocellulose carrier sheet. The carrier sheet is saturated with an excess of non-reactive protein e.g., with bovine serum albumin) or detergent (e.g., Tween ®-20) before it is mounted in the templet 10. The carrier sheet, illustratively shown at 39 in FIG. 5, is then mounted on the central portion 19 of the lower plate 11 with the antigen coated side facing upwardly. The upper plate 12 is then placed over the lower plate 11 with the inner surface 20 facing the carrier sheet and with the channels 22 positioned to extend over the carrier sheet and aligned with the direction of antigen transport during the preparative style gel electrophoresis. The holes 14 and 15 in the upper and lower plates are then aligned and the screws 16 engaged into these holes to tightly press the two plates together at their periphery. The holding screws 16 are also used to clamp the bridge bar 28 in position. The pressure screws 30 are then threaded through the bridge bar into engagement with the top surface of the upper plate 12 and are tightened down hard so that the central area of bottom surface 20, particularly in the land areas 23, is pressed down into very tight engagement with the carrier sheet underneath. Because of this tight engagement, the land areas 23 will press into the nitrocellulose carrier sheet and will prevent migration of any liquid from one channel to another.

Liquids containing the selected particular antibodies are then introduced into the tapered holes 26, as by injection from a pipette. The templet 10 is then incubated for a selected period of time (e.g., 1 to 3 hours), preferably with gentle agitation, such as provided by a rocker table, to distribute the liquids evenly along the length of the channels 22. After incubation, the templet 10 is then tilted toward the end slots 25 and the antibody containing liquids in the channels are aspirated through the holes 25 or withdrawn by pipetting the liquid from the holes 25 with pipette tips or a syringe. After the procedure described above is completed, the screws 16 and 30 are then unscrewed and the upper plate removed from the bottom plate. The treated carrier sheet is then peeled off of the surface of the lower plate 11 and rinsed quickly to remove any unbound antibody. The carrier sheet is now prepared for appropriate immunoblotting procedures in accordance with standard techniques. Generally, at this stage, the carrier sheet is incubated with a tracer antibody solution followed by an appropriate method of detection (e.g., incubation with radiolabeled antibody followed by exposure to X-ray film). After use, the templet 10 may be readily cleaned by rinsing the plates 11 and 12, the screws 16 and 30 and the bar 28 in distilled water.

Figure 7:
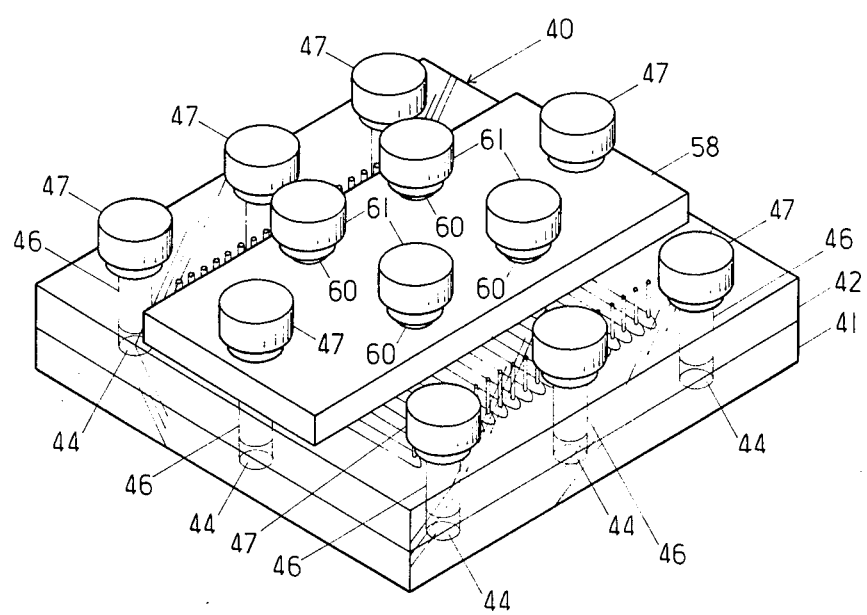
FIG. 7 is an external perspective view of another embodiment of a templet in accordance with the invention.
Figure 8:
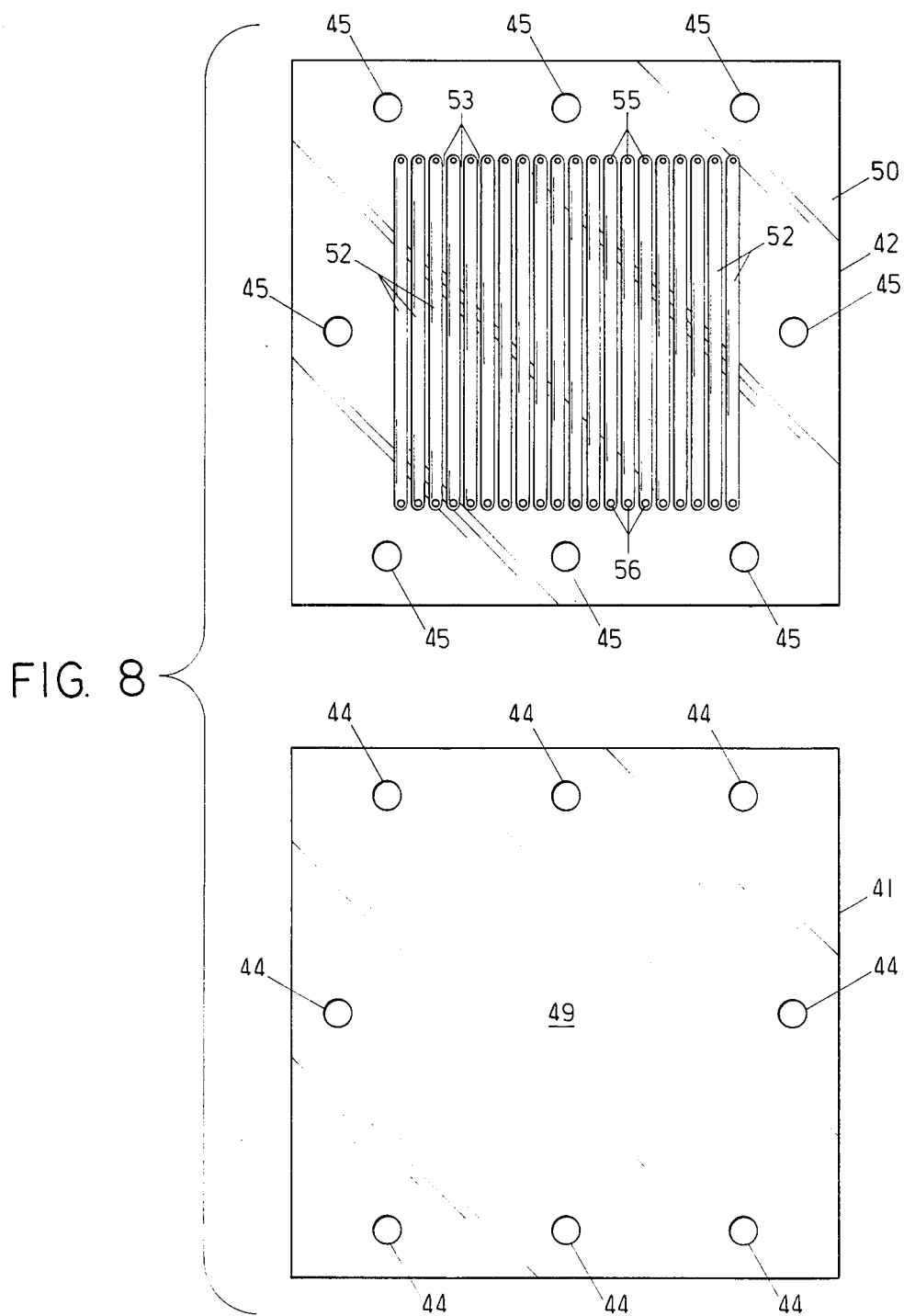
FIG. 8 is a plan view of the upper and lower plates of the templet of FIG. 7.

A somewhat modified embodiment of a templet in accordance with the invention is shown in perspective view at 40 in FIG. 7. The templet 40 is similar in construction to the templet 10, having a lower plate 41, upper plate 42, threaded holes 44 in the lower plate, openings 45 in the upper plate, and holding screws 46 with knurled tops 47 which extend into the peripheral holes 44 and 45. The bottom surface 50 of the upper plate 42 is smooth and flat and has a series of channels 52 formed therein which are separated by land areas 53 coplanar with the surface 50. Tapered holes 55 are drilled through the top plate at one end of the channels 52 and another set of tapered holes 56 are drilled in the upper plate at the opposite end of the channels 52. A wide bridge bar 58, preferably formed of aluminum, is mounted to the top of the upper plate 42 with mounting screws 46, but is wide enough to accommodate four threaded pressure screws 60 having knurled tops 61 which are threaded through the plate 58 to press onto the central area of the top surface of the upper plate. Because of this broader construction of the bridge bar 58, pressure can be applied over a wider area of the upper plate, allowing longer and more closely spaced channels than in the templet 10. For example, 30 or more channels, each ⅛ inch wide, can be formed if desired in the upper plate 42 of the templet 40 and adequate pressure can be applied to the central area of the upper plate so that the land areas 53 are sufficiently tightly engaged against the carrier sheet that leakage of antibody solution between channels does not occur.

It is apparent that the templet of the invention can be formed with more than one set of parallel channels therein. A templet so formed can be used to treat two (or more) carrier sheets simultaneously, or a single carrier sheet on which antigens from two or more gels have been immobilized. For such a templet, the bridge bar or bars span each set of parallel channels to allow pressure to be applied, as by pressure screws, to the upper plate above each set of channels. Such multichannel set templets are particularly suited for use with the electrophoresis performed using smaller polyacrylamide gels (so-called "minigels"), which require lesser amounts of protein samples and shorter time for the electrophoresis procedure.

It is understood that the invention is not confined to the particular construction and arrangement of parts herein illustrated and described, but embraces such modified forms thereof as come within the scope of the following claims.

I claim:

1. A templet for use in screening antibodies immobilized on a carrier sheet, comprising:
   (a) a lower plate having a flat central area on its top surface size to receive a carrier sheet to be laid thereon;
   (b) an upper plate having a flat central area on its bottom surface with a plurality of parallel channels formed therein;
   (c) means for holding the upper plate tightly against the lower plate at peripheral areas outside of the central areas of the upper and lower plates where the carrier sheet is to be laid; and
   (d) means for applying pressure to the upper plate at a position above the parallel channels in the upper plate whereby a carrier sheet engaged between the upper and lower plates will be tightly engaged at the area of the parallel channels, wherein the means for applying pressure to the upper plate includes a bridge bar engaged to at least one of the plates at peripheral positions on either side of the central area of the plates and extending over the parallel channels, and wherein the bridge bar has holes therein at the peripheral ends thereof and including threaded holding screws adapted to pass through the holes in the bridge bar and through corresponding holes in the upper plate and into threaded engagement with threaded holes in the lower plate to firmly hold the bridge bar to the upper plate, and wherein at least one pressure screw is threadingly engaged to a threaded hole in the bridge bar in position to be turned to apply pressure to the area of the top surface of the upper plate above the parallel channels.

2. The templet of claim 1 wherein the upper and lower plates are formed of acrylic plastic.

3. The templet of claim 1 wherein for each of the channels, a hole is formed adjacent to one end of the channel extending from the top surface of the upper plate to the channel and another hole is formed toward the opposite end of each channel extending from the top surface of the upper plate to the channel, whereby a pipette or syringe may be inserted in the holes to allow liquid to be inserted and withdrawn from the channels.

4. The templet of claim 1 wherein at least twenty channels are formed in the upper plate.

5. The templet of claim 1 wherein the means for holding the plates tightly together at the peripheral areas comprises a plurality of holding screws with expanded heads adapted to fit into a plurality of holes formed about the periphery of the upper plate and to be threadingly engaged with a plurality of matching, threaded holes in the lower plate so that the upper and lower plates are tightly held together as the screws are threaded down through the holes in the upper plate into the threaded holes in the lower plate.

6. The templet of claim 5 wherein the holding screws are formed of acetal plastic.

7. The templet of claim 1 wherein the bridge bar is formed of metal in a substantially flat, rectangular shape such that the bridge bar lies substantially flat across the top surface of the upper plate.

8. A method of screening several antibodies simultaneously by immunoblotting, comprising the steps of:
 (a) providing a carrier sheet on which an antigen source is distributed and is immobilized;
 (b) providing a templet having:
  a lower plate having top surface with a flat central area sized to receive the carrier sheet laid flat thereon; and
  an upper plate having a flat bottom surface with a plurality of parallel channels formed therein in the central area thereof adapted to extend over the central area of the lower plate when the upper and lower plate are in facing relation;
  means for holding the upper plate tightly against the lower plate at peripheral areas outside of the central areas of the upper and lower plates where the carrier sheet is to be laid;
  a bridge bar engaged to at least one of the plates at peripheral positions on either side of the central area of the plates and extending over the parallel channels, and means engaged to the bridge bar for pressing the plates together at a position above the parallel channels in the upper plate whereby a carrier sheet engaged between the upper and lower plates will be tightly engaged at the area of the parallel channels;
 (c) positioning the carrier sheet on the central area of the lower plate with the surface of the sheet on which the antigen is immobilized facing upwardly;
 (d) positioning the upper plate in facing relation to the lower plate such that the channels formed in the bottom surface of the upper plate extend over the carrier sheet and are aligned with the direction of antigen distribution on the sheet;
 (e) holding the upper and lower plates together such that the carrier sheet is tightly engaged between the upper and lower plates with the means engaged to the bridge bar pressing the plates together above the parallel channels;
 (f) introducing selected antibody containing liquids into the channels and maintaining the liquids in the channels in contact with the surface of the carrier sheet for a selected period of time; and then
 (g) drawing the antibody containing liquids out of each of the channels; and
 (h) withdrawing the upper plate away from the lower plate and removing the carrier sheet from the lower plate, whereby the carrier sheet may be treated with subsequent immunoblotting protocols to obtain a number of parallel strips showing the antibodies bound to the distributed antigens.

9. The method of claim 8 including, after the step of removing the carrier sheet from the lower plate, rinsing the carrier sheet in distilled water.

10. The method of claim 8 including, after the step of removing the carrier sheet from the lower plate, washing the carrier sheet to remove unbound antibodies and then incubating the carrier sheet with tracer tagged secondary antibodies which will bind to the antibodies bound on the carrier sheet.

11. A templet for use in screening antibodies immobilized on a carrier sheet, comprising:
 (a) a lower plate having a flat central area on its top surface sized to receive a carrier sheet to be laid thereon;
 (b) an upper plate having a flat central area on its bottom surface with a plurality of parallel channels formed therein;
 (c) a plurality of holding screws extending through holes in the upper and lower plates to hold the upper plate tightly against the lower plate at peripheral areas outside of the central areas of the upper and lower plates where the carrier sheet is to be laid; and
 (d) a bridge bar engaged to at least one of the plates at peripheral positions on either side of the central area of the plates and extending over the parallel channels, and means engaged to the bridge bar for pressing the plates together at a position above the parallel channels in the upper plate whereby a carrier sheet engaged between the upper and lower plates will be tightly engaged at the area of the parallel channels.

12. The templet of claim 11 wherein the holding screws have expanded heads which engage the top surface of the upper plate to draw the upper plate toward the lower plate.

13. The templet of claim 11 wherein the bridge bar has holes therein at the peripheral ends thereof and including threaded screws adapted to pass through the holes in the bridge bar and through corresponding holes in the upper plate and into threaded engagement with threaded holes in the lower plate to firmly hold the bridge bar to the upper plate, and wherein the means engaged to the bridge bar for pressing the plates together includes at least one pressure screw threadingly engaged to a threaded hole in the bridge bar in position to be turned to apply pressure to the top surface of the upper plate above the parallel channels.

14. The templet of claim 11 wherein the upper and lower plates are formed of acrylic plastic.

15. The templet of claim 11 wherein the holding screws are formed of acetal plastic.

16. The templet of claim 11 wherein for each of the channels, a hole is formed adjacent to one end of the channel extending from the top surface of the upper plate to the channel and another hole is formed toward the opposite end of each channel extending from the top surface of the upper plate to the channel, whereby a pipette or syringe may be inserted in the holes to allow liquid to be inserted and withdrawn from the channels.

17. The templet of claim 11 wherein at least twenty channels are formed in the upper plate.

18. The templet of claim 11 wherein the bridge bar is formed of metal in a substantially flat, rectangular shape such that the bridge bar lies substantially flat across the top surface of the upper plate.

* * * * *